United States Patent
Wennerholm et al.

(10) Patent No.: US 6,818,665 B2
(45) Date of Patent: Nov. 16, 2004

(54) TREATMENT OF OBSTRUCTIVE SLEEP APNEA

(76) Inventors: Bjorn Wennerholm, N. Krokslattsgatan 2, S-412 64 Gothenburg (SE); Jim Enkvist, Thornburnagatan 5A, S-412 64 Gothenburg (SE)

( * ) Notice: Subject to any disclaimer, the term of this patent is extended or adjusted under 35 U.S.C. 154(b) by 0 days.

(21) Appl. No.: 10/248,727

(22) Filed: Feb. 12, 2003

(65) Prior Publication Data

US 2004/0157813 A1 Aug. 12, 2004

(51) Int. Cl.[7] .......................... A61K 31/405; A61K 31/56
(52) U.S. Cl. ........................................ 514/415; 514/171
(58) Field of Search ................................ 514/415, 171

(56) References Cited

U.S. PATENT DOCUMENTS

| 4,680,289 A | * | 7/1987 | Applezweig | 514/172 |
| 6,048,846 A | * | 4/2000 | Cochran | 514/168 |

* cited by examiner

*Primary Examiner*—Sreeni Padmanabhan
*Assistant Examiner*—Jennifer Kim
(74) *Attorney, Agent, or Firm*—Rolf Fasth; Fasth Law Offices

(57) ABSTRACT

The method is for a hormonal treatment to compensate for the weakening of farynx components, tongue, tonsils, uvula, soft palate that occur during deep sleep and blocks the airways to cause obstructive sleep apnea. About 0.5–5 mg of melatonin is orally administered to a person between 10–80 years old before the person sleeps anddehydroepiandrosterone (DHEA) is administered in combination with andrenocorticotropic hormone (ACTH).

4 Claims, No Drawings

TREATMENT OF OBSTRUCTIVE SLEEP APNEA

BACKGROUND OF INVENTION

During the 1970s, when the so called pulse-oximetric devices for the determination of oxygen-gas saturation in arterial blood, were starting to be used more generally within the healthcare industry, it was observed that the sleeping patients snored intermittently with substantial lowering of SpO2 during the breathing interruptions. The SpO2 variation during the entire sleeping period was determined. This was done by the non-invasive measuring of the blood color by letting light shine through a finger tip. The result was that about one in hundred patients had between 200–400 breathing interruptions that could last about ½ to 1 minute with a de-saturation level of 40% from the normal 90% level. Parallel measurements of the pulse, blood pressure, EKG and CO2 showed substantial variations that were almost of an life threatening character.

From being treated as a mere social problem, such as mainly disturbing to spouses with sound levels of over 90 dB at a sleeping distance of about 0.5 to 1 meters, hitherto unknown consequences to the snoring person were discovered during the 1980–90s. Heart disorders, diabetes, lowering of intelligence, worsened memory, and DAMP/adhd have shown to be connected to obstructive sleeping apnea (OSA). Also a large number of traffic accidents are a result of micro-sleeping attacks while the person is driving. This causes more accidents than DWI since sleeping drivers who are driving on the wrong side do not react.

Because about 80000 drivers in Sweden alone are thought to be affected by OSA, many attempts have been made to prevent accidents from occurring and to improve the health of apnea patients. UPPP surgery, jaw adjusting inserts and the use of over-pressure treatment with a face mask during sleep that requires electricity powered air pumps (fans), such as continuous positive airway pressure (CPAP) equipment, have been used. This is relatively expensive, uncomfortable, cumbersome and not attractive steps. The attempts to develop medical treatment methods have not been successful despite efforts for 20 years. There is a need for an effective method of treating OSA that is reliable, inexpensive and effective.

SUMMARY OF INVENTION

The present invention provides a solution of the above-outlined problems. More particularly, the method of the present invention is for a hormonal treatment to compensate for the weakening of farynx components, tongue, tonsils, uvula, soft palate that occur during sleep and blocks the airways to cause obstructive sleep apnea. About 0.5–5 mg of melatonin is orally administered to a person between 10–80 years old before the person sleeps and dehydroepiandrosteron (DHEA) is simultaneously administered in combination with andrenokortikotropt hormone (ACTH).

DETAILED DESCRIPTION

The medical treatment of OSA must be effective, inexpensive and without any side effects because it must be ongoing for the rest of the patient's life during the sleeping period regardless of the time of the day or night. By conducting regular oximeter tests in connection with the fitting of mechanical assistance, it has been concluded that anti-oxidants, such as tokoferole, has some effect. Hormones that govern the sleep initiation during for example, jet lag, such melatonin that is formed in a gland from the amino-acid tryptophane with serotonin as an intermediate step. When melatonin (5-metoxy-N-acetyletryptamine) is taken in a low dose 0.5–5 mg depending on the patient's age in the range 10–80 years, a distinct effect on the sleeping registration of OSA patients have been established in the form of reduced number of desaturations and the level of SpO2 reduction below 90%. Melatonin is a "downer" and has a long term effect and provides an optimal effect after a couple of weeks of regular intake. The corresponding effect has been noticed when the intake has stopped and this effect is normally quicker.

The parallel intake of another stimulant such as a DHEA (dehydroepiandrosterone) hormone provides a synergistic increase of the desired effect as described above especially in combination with the hormone ACTH that stimulates DHEA. DHEA prevents unwanted complete or total (100%) relaxation of the muscles in the throat region caused melatonin. DHEA stimulates those muscles, including farynx components, tongue, tonsils, uvula, soft palate, so that the tongue and other components do not interfere with the breathing during sleep. ACTH may be used to increase the production of DHEA. Melatonin may be taken as tablets and lasts about 24 hours. Preferably, melatonin is taken at night. A suitable melatonin dose may be about 0.5–5 mg. DHEA may also be taken as tablets and lasts about 24 hours. Preferably, DHEA is taken in the morning. A suitable DHEA dose may be about 1–5 mg. Of course, melatonin and DHEA may be administered at other times of the day.

While the present invention has been described in accordance with preferred compositions and embodiments, it is to be understood that certain substitutions and alterations may be made thereto without departing from the spirit and scope of the following claims.

What is claimed is:

1. A method for hormonal treatment of obstructive sleep apnea to a patient in need thereof by compensating for relaxation of muscles in a throat region including pharynx components, tongue, tonsils, uvula, soft palate that occur during deep sleep and blocks airways to cause obstructive sleep apnea, comprising:

orally adinistering 0.5–5 mg of melatonin to the patient before the patient sleeps; and administering 1–5 mg dehydroepiandrostercne (DHEA) to the patient in need thereof to prevent relaxed muscles in the throat region from interfering with the patient's breathing during the patient's sleep.

2. The method according to claim 1 wherein the method further comprises combining DHEA with an andrenocorticotropic hormone (ACTH) for stimulating DHEA.

3. The method according to claim 1 wherein the method further comprises administering the melatonin at night and DHEA in the mornings.

4. A method for hormonal treatment of obstructive sleep apnea by compensating for relaxation of muscles in a throat region including pharynx components, tongue, tonsils, uvula, soft palate that occur during deep sleep and blocks airways to cause obstructive sleep apnea, comprising:

orally administering 0.5–5 mg of melatonin to a patient in need thereof before the patient sleeps;

administering 1–5 mg of dehydroepiandrosterone (DHEA) to the patient in need thereof in an amount sufficient to prevent relaxed muscles in the throat region from interfering with the patient's breathing during the patient's sleep; and simultaneously with the DHEA, administering an andrenocorticotropic hormone (ACTH) to the patent in need thereof to increase a production of DHEA.

* * * * *